(12) United States Patent
Yokhin et al.

(10) Patent No.: US 6,895,075 B2
(45) Date of Patent: May 17, 2005

(54) X-RAY REFLECTOMETRY WITH SMALL-ANGLE SCATTERING MEASUREMENT

(75) Inventors: Boris Yokhin, Nazareth Illit (IL); Alexander Dikopoltsev, Haifa (IL); Tzachi Rafaeli, Givat Shimshit (IL); Amos Gvirtzman, Moshav Zippori (IL)

(73) Assignee: Jordan Valley Applied Radiation Ltd., Migdal Haemek (IL)

( * ) Notice: Subject to any disclaimer, the term of this patent is extended or adjusted under 35 U.S.C. 154(b) by 162 days.

(21) Appl. No.: 10/364,883

(22) Filed: Feb. 12, 2003

(65) Prior Publication Data

US 2004/0156474 A1 Aug. 12, 2004

(51) Int. Cl.⁷ ............. G01N 23/201; G01N 23/203
(52) U.S. Cl. ............. 378/90; 378/70; 378/86; 378/88; 378/89
(58) Field of Search ............. 378/44, 45, 46, 378/50, 70, 86, 88, 89, 90; 356/237.2, 237.3, 237.4, 237.5

(56) References Cited

U.S. PATENT DOCUMENTS

| | | | |
|---|---|---|---|
| 4,725,963 A | 2/1988 | Taylor et al. | 364/507 |
| 5,151,588 A | 9/1992 | Kiri et al. | 250/208.1 |
| 5,574,284 A | 11/1996 | Farr | 250/370.06 |
| 5,619,548 A | 4/1997 | Koppel | 378/70 |
| 5,740,226 A | 4/1998 | Komiya et al. | 378/70 |
| 5,923,720 A | 7/1999 | Barton et al. | 378/84 |
| 5,949,847 A * | 9/1999 | Terada et al. | 378/90 |
| 6,192,103 B1 * | 2/2001 | Wormington et al. | 378/73 |
| 6,381,303 B1 | 4/2002 | Vu et al. | 378/46 |
| 6,389,102 B2 | 5/2002 | Mazor et al. | 378/89 |
| 6,453,006 B1 | 9/2002 | Koppel et al. | 378/86 |
| 6,507,634 B1 | 1/2003 | Koppel et al. | 378/54 |
| 6,512,814 B2 | 1/2003 | Yokhin et al. | 378/82 |
| 6,643,354 B2 | 11/2003 | Koppel et al. | 378/86 |
| 6,711,232 B1 * | 3/2004 | Janik | 378/70 |
| 6,744,950 B2 | 6/2004 | Aleksoff | 385/48 |
| 6,771,735 B2 * | 8/2004 | Janik et al. | 378/70 |
| 2001/0028699 A1 | 10/2001 | Iwasaki | 378/84 |
| 2001/0043668 A1 | 11/2001 | Hayashi et al. | 378/89 |
| 2002/0097837 A1 | 7/2002 | Fanton et al. | 378/82 |
| 2002/0110218 A1 | 8/2002 | Koppel et al. | 378/86 |
| 2003/0157559 A1 * | 8/2003 | Omote et al. | 435/7.1 |
| 2004/0052330 A1 | 3/2004 | Koppel et al. | 378/46 |

OTHER PUBLICATIONS

Chihab et al., "New Apparatus for Grazing X–Ray Reflectometry in the Angle–Resolved Dispersive Mode", Journal of Applied Crystallography 22 (1989), p. 460.

XTF5011 Tube, Produced by Oxford Instruments of Scotts Valley, California. Jun. 1999.

Doubly–Bent Focusing Crystal Optic, Produced by XOS Inc., of Albany, New York. Jul. 2000.

Wiener et al., "Characterization of Titanium Nitride Layers by Grazing–Emission X–Ray Fluorescence Spectrometry", in Applied Surface Science 125 (1998), p. 129.

Model S7032–0908N array, Produced by Hamamatsu, of Hamamatsu City, Japan. May 2000.

(Continued)

Primary Examiner—Allen C. Ho
(74) Attorney, Agent, or Firm—Weingarten, Schurgin, Gagnebin & Lebovici LLP

(57) ABSTRACT

Apparatus for inspection of a sample includes a radiation source and an array of detector elements arranged to receive radiation from the surface due to irradiation of an area of the surface by the radiation source. The array has a first operative configuration for resolving the received radiation along a first axis perpendicular to the surface, and a second operative configuration for resolving the received radiation along a second axis parallel to the surface. A signal processor processes the signal from the detector array in the two configurations so as to determine a reflectance of the surface as a function of elevation angle relative to the surface and a scattering profile of the surface as a function of azimuthal angle in a plane of the surface.

23 Claims, 7 Drawing Sheets

OTHER PUBLICATIONS

J. Spear, "Metrology for low–k materials", Silknet Aliance, 2003.

J.R. Levine Parrill, et al, "GISAXS—Glancing Incidence Small Angle X–ray Scattering", Journal de Physique IV 3 (Dec. 1993), pp. 411–417.

Jaklevic, et al., "High Rate X–Ray Fluorescence Analysis by Pulsed Excitation", IEEE Transactions on Nuclear Science NS–19:3 (1972), pp. 392–395.

Jaklevic, et al., "Small X–Ray Tubes for Energy Dispersive Analysis Using Semiconductor Spectrometers", Advances in X–Ray Analysis 15 (1972), pp. 266–275.

Jaklevic, et al., "Energy Dispersive X–Ray Fluorescence Spectrometry Using Pulsed X–Ray Excitation", Advances in X–Ray Analysis 19 (1976).

Wormington, Characterization of Pore Size Distribution in Low k Dielectrics Using X–ray Reflectivity, presented at the Sematech Gate Stack Engineering Workshop (Austin, Texas, May 2, 2002).

Ito, "X–ray Scattering Method for Determining Pore–Size Distribution in Low–k Thin Films", Presented at the International Sematech Ultra–Low–k Workshop (San Francisco, CA, Jun. 6–7, 2002).

N. Wu, et al, "Substepping and its Application to HST Imaging", Jul. 28, 2003.

* cited by examiner-

X-RAY REFLECTOMETRY WITH SMALL-ANGLE SCATTERING MEASUREMENT

CROSS-REFERENCE TO RELATED APPLICATION

This application is related to U.S. patent application Ser. No. 09/833,902, which was filed Apr. 12, 2001, and was published Oct. 17, 2002, as U.S. Patent Application Publication US 2002/0150208 A1, now U.S. Pat. No. 6,512,814 B2. This related application is assigned to the assignee of the present patent application, and its disclosure is incorporated herein by reference.

FIELD OF THE INVENTION

The present invention relates generally to analytical instruments, and specifically to instruments and methods for thin film analysis using X-rays.

BACKGROUND OF THE INVENTION

X-ray reflectometry (XRR) is a well-known technique for measuring the thickness, density and surface quality of thin film layers deposited on a substrate. Conventional X-ray reflectometers are sold by a number of companies, among them Technos (Osaka, Japan), Siemens (Munich, Germany) and Bede Scientific Instrument (Durham, UK). Such reflectometers typically operate by irradiating a sample with a beam of X-rays at grazing incidence, i.e., at a small angle relative to the surface of the sample, near the total external reflection angle of the sample material. Measurement of X-ray intensity reflected from the sample as a function of angle gives a pattern of interference fringes, which is analyzed to determine the properties of the film layers responsible for creating the fringe pattern. The X-ray intensity measurements are commonly made using a position-sensitive detector, such as a proportional counter or an array detector, typically a photodiode array or charge-coupled device (CCD).

A method for analyzing the X-ray data to determine film thickness is described, for example, in U.S. Pat. No. 5,740,226, to Komiya et al., whose disclosure is incorporated herein by reference. After measuring X-ray reflectance as a function of angle, an average reflectance curve is fitted to the fringe spectrum. The average curve is based on a formula that expresses attenuation, background and surface roughness of the film. The fitted average reflectance curve is then used in extracting the oscillatory component of the fringe spectrum. This component is Fourier transformed to find the film thickness.

U.S. Pat. No. 5,619,548, to Koppel, whose disclosure is incorporated herein by reference, describes an X-ray thickness gauge based on reflectometric measurement. A curved, reflective X-ray monochromator is used to focus X-rays onto the surface of a sample. A position-sensitive detector, such as a photodiode detector array, senses the X-rays reflected from the surface and produces an intensity signal as a function of reflection angle. The angle-dependent signal is analyzed to determine properties of the structure of a thin film layer on the sample, including thickness, density and surface roughness.

U.S. Pat. No. 5,923,720, to Barton et al., whose disclosure is incorporated herein by reference, also describes an X-ray spectrometer based on a curved crystal monochromator. The monochromator has the shape of a tapered logarithmic spiral, which is described as achieving a finer focal spot on a sample surface than prior art monochromators. X-rays reflected or diffracted from the sample surface are received by a position-sensitive detector.

XRR may also be used in situ, within a deposition furnace, to inspect thin film layers in production on a semiconductor wafer, as described, for example, by Hayashi et al., in U.S. Patent Application Publication US 2001/0043668 A1, whose disclosure is incorporated herein by reference. The furnace is provided with X-ray incidence and extraction windows in its side walls. The substrate upon which the thin film has been deposited is irradiated through the incidence window, and the X-rays reflected from the substrate are sensed through the X-ray extraction window.

Small-angle X-ray scattering (SAXRS) is another method for surface layer characterization. It is described, for example, by Parrill et al., in "GISAXS—Glancing Incidence Small Angle X-ray Scattering," *Journal de Physique IV* 3 (December, 1993), pages 411–417, which is incorporated herein by reference. In this method, an incident X-ray beam is totally externally reflected from a surface. The evanescent wave within the surface region is scattered by microscopic structures within the region. Measurement of the scattered evanescent wave can provide information about these structures. For example, Parrill et al. describe the use of this technique for determining size information regarding islands associated with film growth on the surface.

SAXRS can be used in this manner to determine characteristics of pores in a surface layer of a low-k dielectric material formed on a silicon wafer. Nano-porous silicates and polymers are considered to be attractive materials for use in microelectronic devices with sub-0.25 $\mu$m technology, but non-destructive characterization of pore size and density has so far proved to be a difficult task. The use of diffuse X-ray reflectivity in characterizing porous low-k materials is described, for example, by Wormington in "Characterization of Pore Size Distribution in Low k Dielectrics Using X-ray Reflectivity," presented at the Sematech Gate Stack Engineering Workshop (Austin, Tex., May 2, 2002), which is incorporated herein by reference. A similar method is described by Ito in "X-ray Scattering Method for Determining Pore-Size Distribution in Low-k Thin Films," presented at the International Sematech Ultra Low-k Workshop (San Francisco, Calif., Jun. 6–7, 2002), which is also incorporated herein by reference.

The configuration of X-ray optics used to irradiate a sample under evaluation by SAXRS is typically different from that used in XRR. For example, Iwasaki describes an X-ray optical device and multilayer mirror for use in a small angle scattering system in U.S. Patent Application Publication US 2001/0028699 A1, now U.S. Pat. No. 6,504,902 B2, whose disclosure is incorporated herein by reference. The multilayer mirror has elliptical reflection faces, which have two focal points. Thus, an X-ray beam from a source at one of the focal points is focused to a spot at the other focal point in a manner that is said to provide high precision in small-angle scattering measurements.

SUMMARY OF THE INVENTION

The present invention provides methods and systems for performing combined XRR and SAXRS measurements on a sample. These methods and systems are advantageous, for example, in characterizing porous materials, such as low-k porous dielectrics. Although XRR and SAXRS are complementary, in terms of the information they provide, there are difficulties inherent in performing both types of measurements using a single system. In terms of irradiation of the sample, for precise measurement of SAXRS, a collimated beam is advantageous. On the other hand, XRR may advantageously use a converging beam with a large convergence angle, so that reflectivity measurements may be made over a range of several degrees simultaneously. On the detection side, SAXRS typically looks at scattering as a function of azimuth, within the surface plane of the sample, while XRR is based on measuring reflected X-rays as a function of elevation, perpendicular to the surface plane.

Embodiments of the present invention use novel X-ray optics and detection assemblies to serve the needs of both XRR and SAXRS conveniently and efficiently. In these embodiments, X-ray inspection apparatus comprises a radiation source, which is configured to irradiate a small area on a surface of a sample. The X-ray optics control the radiation beam so as to adjust the angular width and height of the beam, depending on the type of measurement being performed. The detection assembly comprises an array of detector elements, which is positioned to receive radiation that is reflected or scattered from the irradiated area. The array has two operative configurations: one in which the elements of the array resolve the radiation along a first axis, perpendicular to the plane of the sample, and another in which the elements resolve the radiation along a second axis, parallel to the plane. The appropriate configuration is selected, mechanically or electronically, for the type of measurement being performed. Typically, the first axis is selected for XRR measurements, and the second axis is selected for SAXRS.

Although the embodiments of the present invention described herein are directly mainly toward enhancing X-ray measurements on thin films, and particularly on films formed on semiconductor wafers, the principles of the present invention can similarly be used in other applications of X-ray reflectometry and scattering, such as analysis of colloids, as well as in other types of radiation-based analysis.

There is therefore provided, in accordance with an embodiment of the present invention, apparatus for inspection of a sample, including:

a radiation source, which is adapted to irradiate an area on a surface of the sample;

a detector assembly, including an array of detector elements arranged to receive radiation from the surface due to irradiation of the area by the radiation source and to generate a signal responsive to the received radiation, the array having a first operative configuration for resolving the received radiation along a first axis perpendicular to the surface, and a second operative configuration for resolving the received radiation along a second axis parallel to the surface; and a signal processor, which is coupled to process the signal from the detector assembly in the first configuration so as to determine a reflectance of the surface as a function of elevation angle relative to the surface, and to process the signal from the detector assembly in the second configuration so as to determine a scattering profile of the surface as a function of azimuthal angle in a plane of the surface.

Typically, the radiation source includes an X-ray source which is adapted to emit a beam of X-rays toward the area, and the apparatus includes X-ray optics, which are adapted to adjust a transverse dimension of the beam depending upon whether the array is in the first or the second operative configuration. The X-ray optics may be adapted to adjust the beam so as to define a cone of rays, converging on the area on the surface of the sample, when the array is in the first operative configuration, and to substantially collimate the beam when the array is in the second operative configuration.

Additionally or alternatively, the X-ray optics include a shutter assembly, which is adjustable so as to adjust a range of angles, relative to the surface of the sample, within which the beam of X-rays is incident on the surface. Typically, the signal processor is adapted to determine the scattering profile due to a surface layer that overlies a substrate of the sample, and the shutter assembly is adjustable so that the range of angles within which the beam of X-rays is incident on the surface is approximately bounded by a first critical angle for total external reflection from the surface layer and by a second critical angle for total external reflection from the substrate, wherein the second critical angle is greater than the first critical angle.

In an embodiment of the present invention, the array of detector elements has an array axis, and the array is rotatable so that the array axis is perpendicular to the surface in the first operative configuration, and the array axis is parallel to the surface in the second operative configuration. The array may include a linear array, and the detector elements may have a transverse dimension, perpendicular to the array axis, that is substantially greater than a pitch of the array. Alternatively, the array may include a two-dimensional matrix of the detector elements, and the detector assembly may be adapted to bin the detector elements in respective rows of the array along a direction perpendicular to the array axis.

In an embodiment of the present invention, the signal processor is adapted to determine the reflectance and the scattering profile due to a porous surface layer that overlies a substrate of the sample, and to estimate, based on the reflectance and the scattering profile, one or more characteristics of pores located within the porous surface layer. Typically, the one or more characteristics include a density and average size of the pores.

There is also provided, in accordance with an embodiment of the present invention, a method for inspection of a sample, including:

irradiating an area on a surface of the sample;

configuring an array of detector elements in a first operative configuration to receive radiation from the surface due to irradiation of the area by the radiation source while resolving the received radiation along a first axis perpendicular to the surface, so as to generate a first signal responsive to the received radiation;

configuring the array of detector elements in a second operative configuration to receive the radiation from the surface due to irradiation of the area by the radiation source while resolving the received radiation along a second axis parallel to the surface, so as to generate a second signal responsive to the received radiation;

processing the first signal so as to determine a reflectance of the surface as a function of elevation angle relative to the surface; and processing the second signal so as to determine a scattering profile of the surface as a function of azimuthal angle in a plane of the surface.

In one embodiment, irradiating the area includes irradiating a semiconductor wafer within a chamber used to deposit a thin-film layer on the surface of the wafer, and configuring the array of detector elements in the first and second operative configurations includes receiving the radiation from the surface of the wafer within the chamber.

There is additionally provided, in accordance with an embodiment of the present invention, a cluster tool for producing microelectronic devices, including:

a deposition station, which is adapted to deposit a thin-film layer on a surface of a semiconductor wafer;

an inspection station, including:

a radiation source, which is adapted to irradiate an area on the surface of the wafer; and a detector assembly, including an array of detector elements-arranged to receive radiation from the surface due to irradiation of the area by the radiation source and to generate a signal responsive to the received radiation, the array having a first operative configuration for resolving the received radiation along a first axis perpendicular to the surface, and a second operative configuration for resolving the received radiation along a second axis parallel to the surface; and a signal processor, which is coupled to process the signal from the detector assembly in the first configuration so as to determine a reflectance of the surface as a function of elevation angle relative to the surface, and to process the signal from the detector assembly in the second configuration so as to determine a scattering profile of the surface as a function of azimuthal angle in a plane of the surface, so as to assess a quality of the thin-film layer deposited by the deposition station.

There is furthermore provided, in accordance with an embodiment of the present invention, apparatus for producing microelectronic devices, including:

a production chamber, which is adapted to receive a semiconductor wafer;

a deposition device, which is adapted to deposit a thin-film layer on a surface of the semiconductor wafer within the chamber;

a radiation source, which is adapted to irradiate an area on the surface of the wafer within the chamber;

a detector assembly, including an array of detector elements arranged to receive radiation from the surface due to irradiation of the area by the radiation source and to generate a signal responsive to the received radiation, the array having a first operative configuration for resolving the received radiation along a first axis perpendicular to the surface, and a second operative configuration for resolving the received radiation along a second axis parallel to the surface; and a signal processor, which is coupled to process the signal from the detector assembly in the first configuration so as to determine a reflectance of the surface as a function of elevation angle relative to the surface, and to process the signal from the detector assembly in the second configuration so as to determine a scattering profile of the surface as a function of azimuthal angle in a plane of the surface, so as to assess a quality of the thin-film layer deposited by the deposition device.

The present invention will be more fully understood from the following detailed description of the embodiments thereof, taken together with the drawings in which:

DETAILED DESCRIPTION OF EMBODIMENTS

Figure 1:
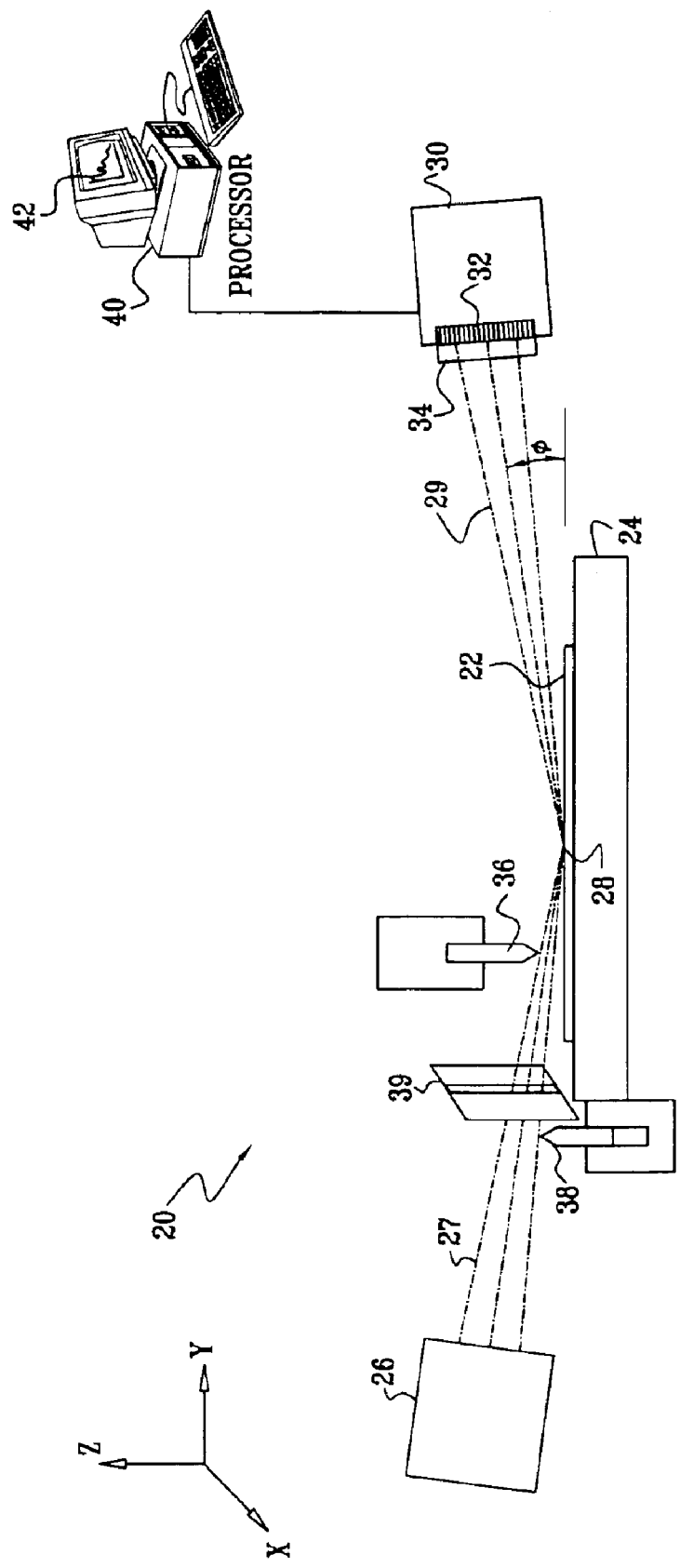
FIG. 1 is a schematic side view of a system for X-ray reflectometry and scattering measurements, in accordance with an embodiment of the present invention.
Figure 2:
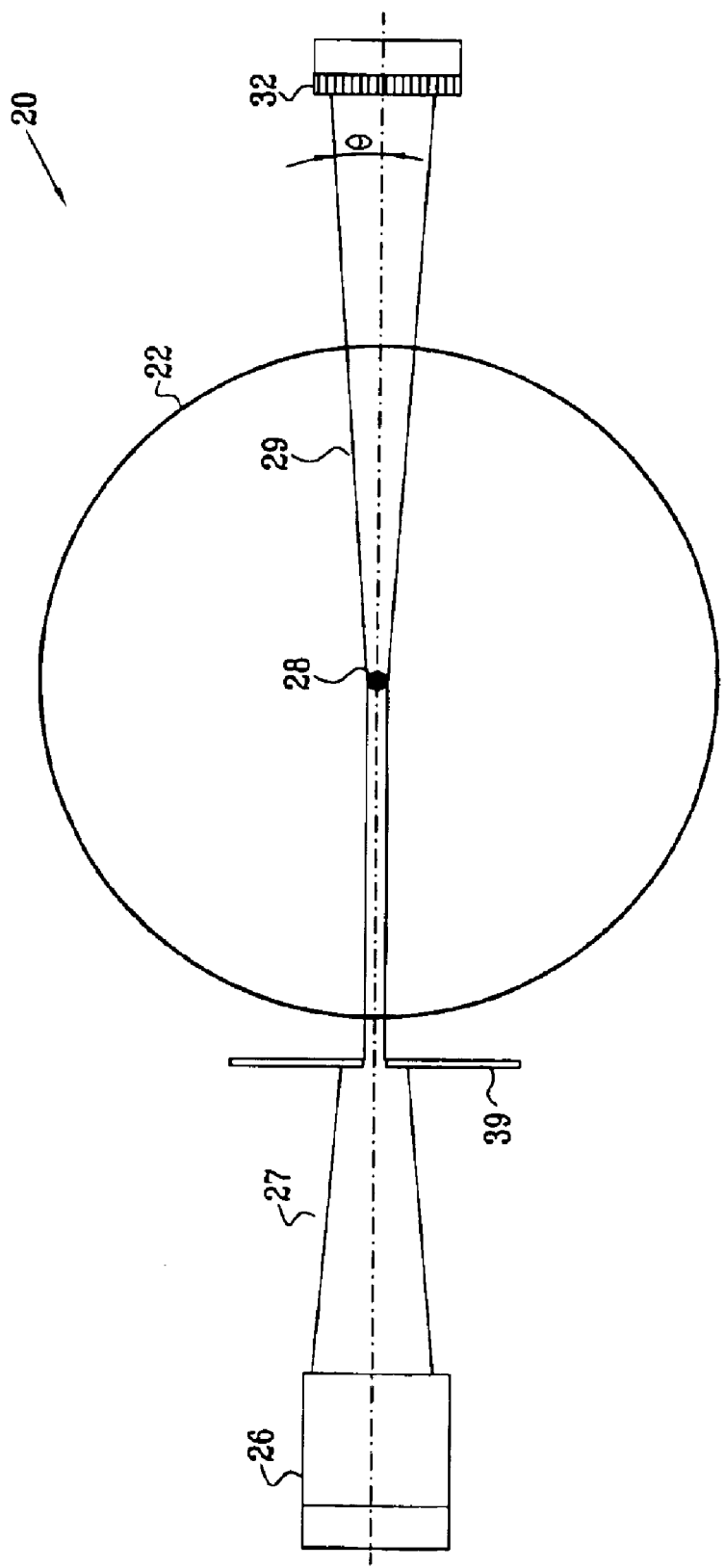
FIG. 2 is a schematic top view of the system of FIG. 1, in a configuration used for SAXRS measurement.

Reference is now made to FIGS. 1 and 2, which schematically illustrate a system 20 for X-ray reflectometry (XRR) and small-angle scattering (SAXRS) measurements, in accordance with an embodiment of the present invention. FIG. 1 is a side view of the system, while FIG. 2 is a top view. System 20 is similar to the XRR system described in the above-mentioned U.S. patent application Ser. No. 09/833,902, now U.S. Pat. No. 6,512,814 B2, with the addition of features and capabilities required for SAXRS measurement.

A sample 22, such as a semiconductor wafer, to be evaluated by system 20 is mounted on a motion stage 24, allowing accurate adjustment of its position and orientation. An X-ray source 26, typically an X-ray tube with suitable monochromatizing optics (not shown), irradiates a small area 28 on sample 22. For example, the XTF50ll X-ray tube, produced by Oxford Instruments (Scotts Valley, Calif.), may be used for this purpose. The optics focus the radiation from the X-ray tube onto area 28 in a converging beam 27. A number of different optical configurations that may be used in source 26 are described in U.S. Pat. No. 6,381,303, whose disclosure is incorporated herein by reference. For example, the optics may comprise a curved crystal monochromator, such as the Doubly-Bent Focusing Crystal Optic, produced by XOS Inc., of Albany, N.Y. Other suitable optics are described in the above-mentioned U.S. Pat. Nos. 5,619,548 and 5,923,720. Further possible optical configurations will be apparent to those skilled in the art. A typical X-ray energy for reflectometric and scattering measurements in system 20 is about 8.05 keV (CuKa1). Alternatively, other energies may be used, such as 5.4 keV (CrKa1).

A dynamic knife edge 36 and shutter 38 are used to limit the angular extent of incident beam 27 of the X-rays in the vertical direction (i.e., perpendicular to the plane of sample 22), while a slit 39 may be used to limit the beam horizontally. The knife edge, shutter and slit together serve as a shutter assembly, for adjusting the transverse dimensions of beam 27. The configuration of the shutter assembly in FIGS. 1 and 2 is shown by way of example, and alternative arrangements of X-ray optics for controlling the transverse dimensions of beam 27 in the manner described hereinbelow will be apparent to those skilled in the art and are considered to be within the scope of the present invention.

The use of knife edge 36 and shutter 38 in XRR measurements is described in detail in the above-mentioned U.S. patent application Ser. No. 09/833,902. Briefly, for optimal detection of low-angle reflections, near 0°, shutter 38 is withdrawn outside the extent of incident beam 27, while knife edge 36 is positioned over area 28 and is lowered to reduce the effective vertical cross-section of the beam. As a result, the lateral dimension of the X-ray spot incident on area 28 is reduced. On the other hand, for effective detection of weaker, high-angle reflection, knife edge 36 is withdrawn from beam 27, while shutter 38 is positioned to cut off the low-angle portion of the beam (Alternatively, the shutter may be positioned to cut off the low-angle portion of reflected beam 29.) In this manner, only the high-angle reflections from sample 22 reach the detector array, and not the strong low-angle reflections, thus enhancing the signal/background ratio of the high-angle measurement.

Whereas for XRR measurements, it is advantageous that beam 27 be focused to converge on area 28, SAXRS measurements are preferably made using a narrow incident beam, typically a beam that is approximately collimated. For this purpose, knife edge 36 and shutter 38 are positioned so that in the vertical direction, only a narrow portion of beam 27, below the critical angle for total external reflection of the sample, is incident on area 28. The optimal positioning of the knife edge and shutter for this purpose is described below with reference to FIG. 4. At the same time, slit 39 is closed down to admit only a narrow horizontal range, as shown in FIG. 2. The slit width is chosen so as to optimize the range and resolution of the SAXRS measurement, as described below. The optimal width depends on the characteristics of beam 27, as generated by source 26. (Below a certain width, typically about 100 $\mu$m, no improvement is gained by further decreasing the width.) During XRR measurements, slit 39 is typically wide open, in order to admit the full cone of converging rays and thus increase the signal/noise ratio of the reflectivity measurement.

A reflected and/or scattered beam 29 of X-rays from sample 22 is collected by a detector assembly 30. Typically, for XRR, assembly 30 collects reflected X-rays over a range of reflection angles in the vertical (elevation—$\phi$) direction between about 0° and 3°, both below and above the critical angle of the sample for total external reflection. For SAXRS, assembly 30 collects scattered X-rays over a similar range of angles in the horizontal (azimuth—$\theta$) direction. (For clarity of illustration, the angles shown in the figures are exaggerated, as is the elevation of source 26 and detector assembly 30 above the plane of sample 22 in FIG. 1.)

Assembly 30 comprises a detector array 32, such as a CCD array, as described hereinbelow. Although for simplicity of illustration, only a single row of detectors elements is shown in the figures, with a relatively small number of detector elements, array 32 generally includes a greater number of elements, arranged as either a linear array or a matrix (two-dimensional) array. Assembly 30 further comprises a window 34 made of a suitable X-ray transparent material, such as beryllium, spaced in front of the detector array, between the array and the sample. Further details of the operation of array 32, and particularly of its use in performing both XRR and SAXRS measurements, are described below with reference to FIGS. 3A and 3B.

A signal processor 40 analyzes the output of assembly 30, so as to determine a distribution 42 of the flux of X-ray photons reflected or scattered from sample 22 as a function of angle at a given energy or over a range of energies. Typically, sample 22 has one or more thin surface layers, such as thin films, at area 28, so that distribution 42 as a function of elevation angle exhibits an oscillatory structure due to interference effects among reflected X-ray waves from the interfaces between the layers. The distribution of the scattered X-rays as a function of azimuth is indicative of microstructure, such as pores, in the surface layer of sample 22. Processor 40 analyzes characteristics of the angular distributions in order to determine characteristics of one or more of the surface layers of the sample, such as the thickness, density, surface quality and pore size of the layer, using methods of analysis described hereinbelow.

Figure 3A:
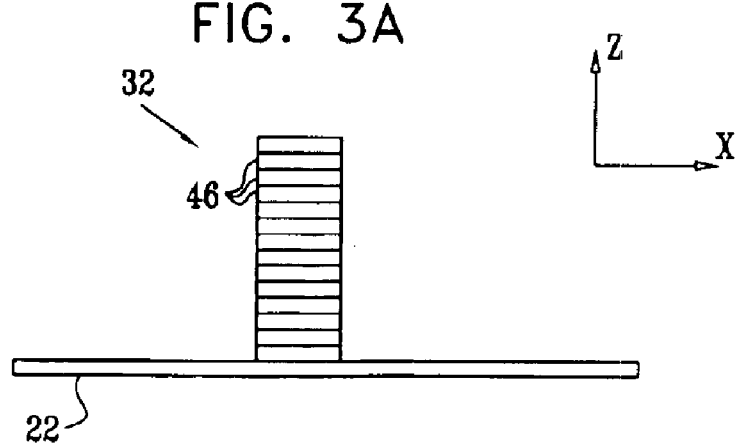
FIGS. 3A and 3B are schematic, frontal views of a detector array, configured for XRR and SAXRS, respectively, in accordance with an embodiment of the present invention.
Figure 3B:
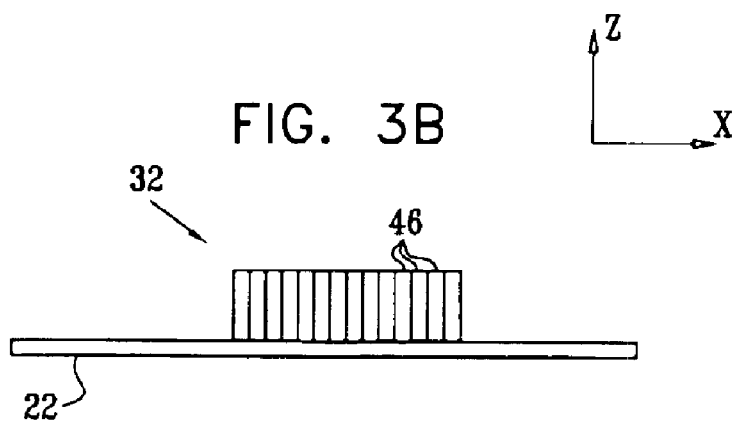

FIGS. 3A and 3B are schematic frontal views of array 32 in first and second operative configurations, respectively, in accordance with an embodiment of the present invention. The first configuration, shown in FIG. 3A, is used for XRR, while the second configuration, shown in FIG. 3B, is used for SAXRS measurements. Array 32 is shown in these figures as comprising a single row of detector elements 46, with an array axis that can be aligned to resolve the incident radiation along either of two axes: a first axis perpendicular to the plane of sample 22, for XRR, and a second axis parallel to the sample plane, for SAXRS. Elements 46 have a high aspect ratio, i.e., their width, in the direction transverse to the array axis, is substantially greater than their pitch along the axes. The high aspect ratio is useful in enhancing the signal/noise ratio of system 20, since array 32 is thus able to collect X-ray photons over a relatively wide area for each angular increment along the array axis. The dimensions of elements 46 are shown in the figures solely by way of example, however, and the principles of the present invention may be applied using elements of smaller or larger aspect ratio, depending on application needs and availability of suitable detector devices.

As noted above, array 32 may comprise either a linear CCD array or a matrix array, such as the model S7032-1008 array produced by Hamamatsu, of Hamamatsu City, Japan. This latter array comprises 1044×256 pixels, with an overall size of 25.4×6 mm. It is capable of being operated in a line-binning mode, using special hardware supplied for this purpose by Hamamatsu, so that multiple detector elements in each row of the array function effectively as a single element with high aspect ratio. In this case, although array 32 physically comprises a two-dimensional matrix of detector elements, functionally the array takes the form of a single line of detector elements, as shown in FIGS. 3A and 3B.

Alternatively, array 32 may comprise an array of PIN diodes with suitable readout circuits, possibly including integrated processing electronics, as described in U.S. Pat. No. 6,389,102, whose disclosure is incorporated herein by reference. This patent also describes alternative features of the array, including various geometrical configurations of the array (both one- and two-dimensional) and masking that may be applied to enhance the array's detection properties. These features are applicable to assembly 30 of the present patent application, as well. In any event, it will be understood that these detector types are described here by way of example, and detectors of any suitable type, dimension and number can be used.

Array 32 may be mechanically switched between the different operative axes of FIGS. 3A and 3B using suitable positioning hardware in assembly 30 (not shown in the figures). Such hardware rotates the array by 90° between the vertical and horizontal axes, depending on the type of measurement being made. If the point of rotation is near the center of array 32, then it may also be necessary to shift the array downward (closer to the plane of sample 22) for SAXRS measurement, and upward for XRR. Alternatively, the point of rotation may be fixed near the plane of the sample, so that no vertical movement of the array is needed. In this case, it may be that in the SAXRS configuration, array 32 will not be centered about the axis of incident beam 27. Since SAXRS is generally symmetrical about the incident beam axis, however, substantially no information is lost by measuring the scattered radiation on one side of the axis, rather than both.

Alternatively, other means may be used for switching between the first and second operative configurations of array 32. For example, if assembly 30 is capable of binning elements 46 of array 32 in both vertical and horizontal directions, then switching between the operative axes may be accomplished electronically, simply by switching the binning direction. While it is also possible, in principle, to mechanically rotate sample 22, this option is not practical for large samples, such as 10–12" semiconductor wafers.

Figure 4:
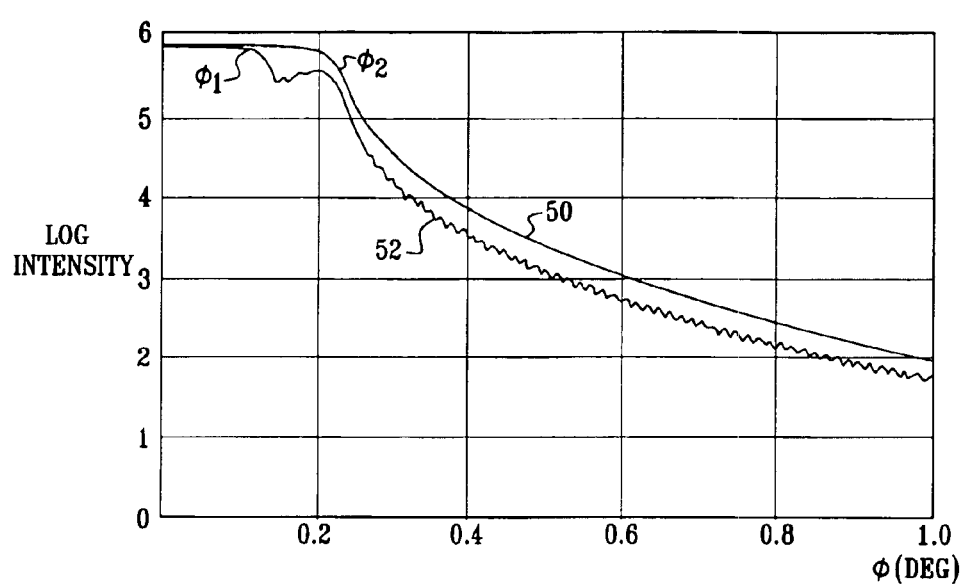
FIG. 4 is a schematic plot of XRR measurements, showing selection of an range of elevation angles to be used for SAXRS measurement, in accordance with an embodiment of the present invention.

FIG. 4 is a schematic plot of XRR measurements made using system 20, in accordance with an embodiment of the present invention. The plot shows the intensity of reflected X-rays received by array 32 as a function of the elevation angle $\phi$. An upper curve 50 shows the reflection measured from a bare silicon wafer, while a lower curve 52 shows the reflection from a wafer on which a low-k porous dielectric film has been formed. Both curves have a shoulder at an angle marked in the figure as $\phi_2$, slightly greater than 0.2°. This angle corresponds roughly to the critical angle for total external reflection from silicon. Above the critical angle, curve 52 shows an oscillatory structure, due mainly to reflections from the upper and lower surfaces of the low-k film. The period and amplitude of this oscillation may be analyzed to determine the thickness and surface quality of the low-k film and possibly other thin film layers below it on the wafer. A Fast Fourier Transform (FFT), for example, may be used to extract the relevant characteristics of the oscillation. Methods for analyzing XRR signals such as curve 52 are described in greater detail in the above-mentioned U.S. patent application Ser. No. 09/833,902.

The critical angle, and hence the location of the shoulder in the reflectance curve, is determined mainly by the density of the material from which the X-rays reflect. Since the porous, low-k dielectric layer that is deposited on the wafer has a substantially lower density than the silicon substrate, the critical angle of the porous layer is substantially smaller than that of the underlying silicon. Therefore, another shoulder is seen in curve 52, at a smaller angle marked in the figure as $\phi_1$, corresponding to the critical angle of the porous layer. Based on the value of $\phi_1$, processor 40 is able to determine the overall density of the porous material. Since the intrinsic density of the dielectric material (in the absence of pores) is typically known, the total volume of pores, per unit volume of the porous layer, may be deduced as the difference between the known, intrinsic density of the dielectric material and the estimated overall density of the porous layer, based on the measured value of $\phi_1$.

The values of $\phi_1$ and $\phi_2$ measured by XRR are also indicative of the optimal settings of knife edge 36 and shutter 38 for making SAXRS measurements. Below $\phi_1$, the X-rays incident on sample 22 do not penetrate substantially into the upper, porous layer, and thus do not contribute significantly to the SAXRS signal. Above $\phi_2$, the incident radiation penetrates into the silicon substrate, so that radiation at these high angles will also not contribute significantly to the SAXRS measurement. Therefore, in preparation for making SAXRS measurements, processor 40 (or an operator of system 20) typically sets the positions of shutter 38 and knife edge 36 so that he shutter cuts off incident radiation at angles below $\phi_1$, while the knife edge cuts off incident radiation at angles above $\phi_2$. Incident radiation outside the range between $\phi_1$ and $\phi_2$ tends only to increase the background due to parasitic scattering from the air and other elements of sample 22 and system 20, without enhancing the SAXRS signal.

Alternatively, instead of dynamically setting the positions of shutter 38 and knife edge 36, a horizontal slit of fixed width may be used to limit the angular range of incident radiation during SAXRS measurements. The inventors have found, for example, that a slit admitting a range of elevation angles between 0.10° and 0.23° relative to the sample surface works well for SAXRS measurements on porous, low-k dielectric films.

Figure 5A:
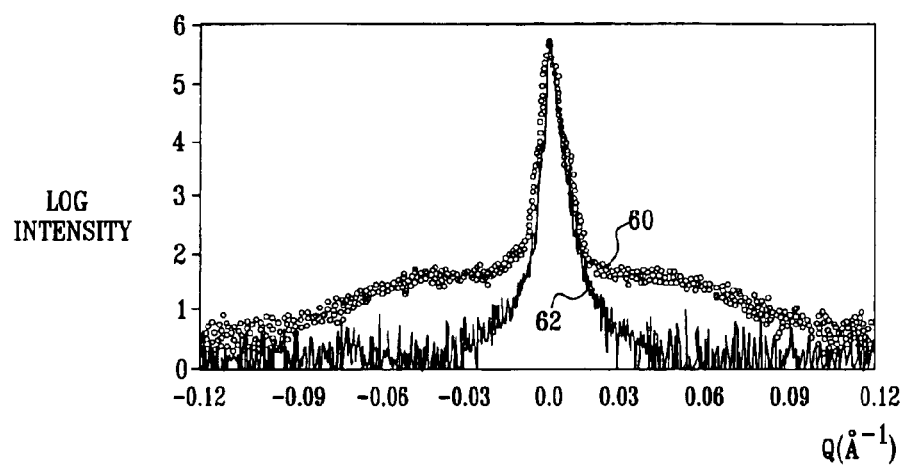
FIG. 5A is a schematic plot of X-ray scattering measured as a function of azimuthal angle for a bare silicon wafer and for a wafer covered by a porous dielectric layer, in accordance with an embodiment of the present invention.

FIG. 5A is a schematic plot of SAXRS measurement results obtained using system 20 in the above-described manner, in accordance with an embodiment of the present invention. The results are displayed as a function of the momentum transfer parameter Q, as is common in the art of X-ray scattering measurement. ($Q = 4\pi \sin\theta/\lambda$, in units of inverse Angstroms, wherein $\theta$ is the azimuth and $\lambda$ is the X-ray wavelength, which was 1.54 Å in the present example.) Two measurements are shown in the figure: an upper curve 60, showing measurement of scatter as a function of Q from a wafer with a porous, low-k upper dielectric layer; and a lower curve 62, showing the scatter from a bare silicon wafer. Curve 60 is normalized according to curve 62, i.e., the amplitude of the entire curve is adjusted so that the central peaks in both curves have equal heights. The effect of scattering from pores in the low-k layer can be appreciated in the elevation of curve 60, relative to curve 62, in the range between about 0.02 Å$^{-1}$ and 0.12 Å$^{-1}$.

Figure 5B:
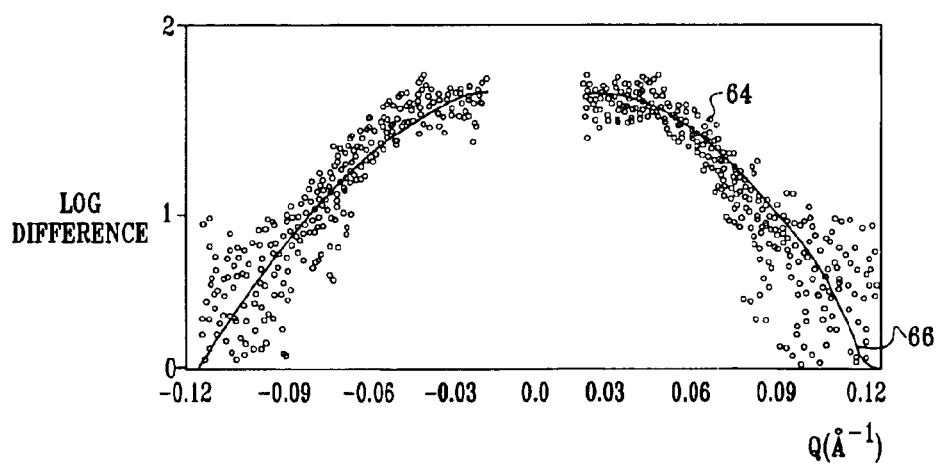
FIG. 5B is a schematic plot showing the difference between the scattering measurements of FIG. 5A and a fit of the difference to a parametric curve, in accordance with an embodiment of the present invention.

FIG. 5B is a schematic plot showing the net SAXRS signal provided by the measurements of FIG. 5A. Data points 64 correspond to the measured difference between curves 60 and 62 at each value of $\theta$. A curve 66 shows a parametric fit to data points 64. The parameters of the fit include the density of the pores C, the average size of the pores $R_0$, and the width of the pore size distribution about the average, $\sigma$. As noted above, the overall porous layer density, and hence the total volume of pores, may be deduced from the XRR measurement shown in FIG. 4. This information may be used as input to the fit of curve 66, in order to obtain an accurate estimate of the average pore size.

Substantially any method of fitting known in the art may be used to fit curve 66 to data points 64. The purpose of the fit is to find values of C, $R_0$, and $\sigma$ that optimally match the distribution of scattered intensity I(Q), as given by the expression:

$$I(Q) = C \int_{Rmin}^{Rmax} dR \cdot [F^2(Q, R)] \cdot n(R) \tag{1}$$

to the experimental results. Here R is the pore size, and $R_{max}$ and $R_{min}$ are heuristic maximum and minimum size limits. F is a scattering form factor given by:

$$F(Q, R) = 3 \cdot V(R) \cdot \frac{\sin(QR) - QR \cdot \cos(QR)}{(QR)^3} \tag{2}$$

assuming spherical pores. The distribution of pore sizes n(R) may be approximated as a normal distribution, in accordance with the Guinier approximation:

$$n(R) = \frac{1}{\sqrt{2\pi} \cdot \sigma} \cdot \exp\left\{-\frac{\left(\frac{R}{R_0} - 1\right)}{2 \cdot \sigma^2}\right\} \tag{3}$$

Alternatively, other distributions may be assumed, such as a log-normal distribution:

$$n(R) = \frac{1}{\sqrt{2\pi} \cdot \sigma \cdot R} \cdot \exp\left\{-\frac{\log^2 \frac{R}{R_0}}{2 \cdot \sigma^2}\right\} \quad (4)$$

Details of the fitting procedure, as well as alternative methods for processing scattering results, will be apparent to those skilled in the art.

As noted above, system 20 is particularly useful in the inspection of thin-film layers formed on semiconductor wafers in the course of fabricating microelectronic devices. For this purpose, system 20 may be deployed as a standalone, off-line inspection station in a semiconductor fabrication facility. Alternatively, inspection systems based on the principles described above may be integrated with semiconductor fabrication equipment for in-line measurement and monitoring. Two examples of in-line systems of this sort are described hereinbelow. Alternative equipment configurations that integrate inspection capabilities in accordance with the principles of the present invention will be apparent to those skilled in the art, upon reading the present patent application, and are considered to be within the scope of the present invention.

Figure 6:
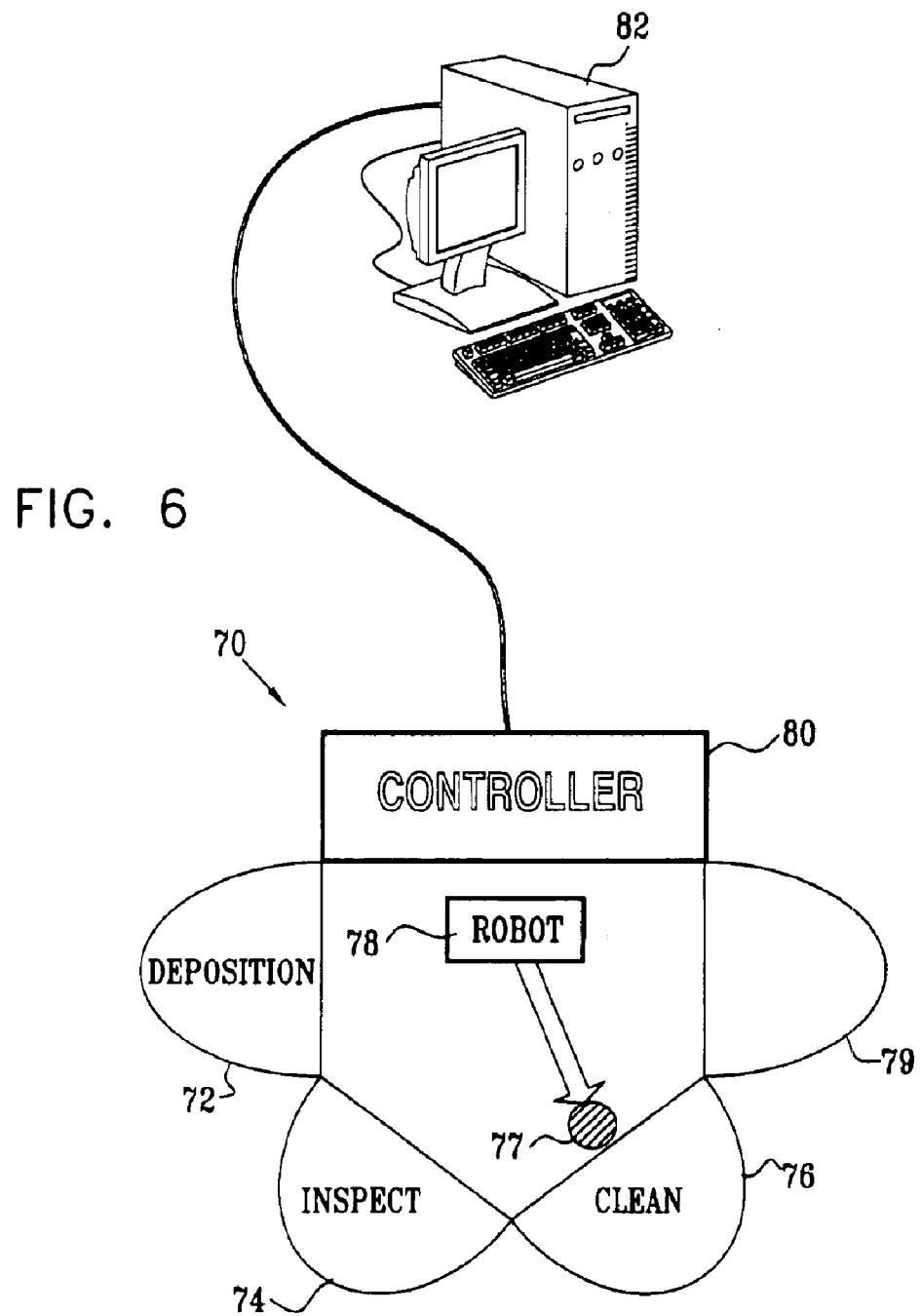
FIG. 6 is a schematic top view of a cluster tool for semiconductor device fabrication, including an inspection station in accordance with an embodiment of the present invention.

FIG. 6 is a schematic top view of a cluster tool 70 for use in semiconductor device fabrication, in accordance with an embodiment of the present invention. The cluster tool comprises multiple stations, including a deposition station 72, for depositing thin films on a semiconductor wafer 77, an inspection station 74, and other stations 76, as are known in the art, such as a cleaning station. Inspection station 74 is constructed and operates in a manner similar to system 20, as described hereinabove. A robot 78 transfers wafer 77 among stations 72, 74, 76, 79, under the control of a system controller 80. Operation of tool 70 may be controlled and monitored by an operator using a workstation 82, coupled to controller 80.

Inspection station 74 is used to perform X-ray inspection of wafers before and after selected steps in production processes carried out by deposition station 72 and other stations in tool 70. The inspection may include either XRR, or SAXRS, or both. In an exemplary embodiment, deposition station 72 is used to create porous thin films, such as porous low-k dielectric layers, on wafer 77, and inspection station 74 performs both XRR and SAXRS evaluation, as described above. This arrangement allows early detection of process deviations and convenient adjustment and evaluation of process parameters on production wafers, using controller 80 and possibly workstation 82.

Figure 7:
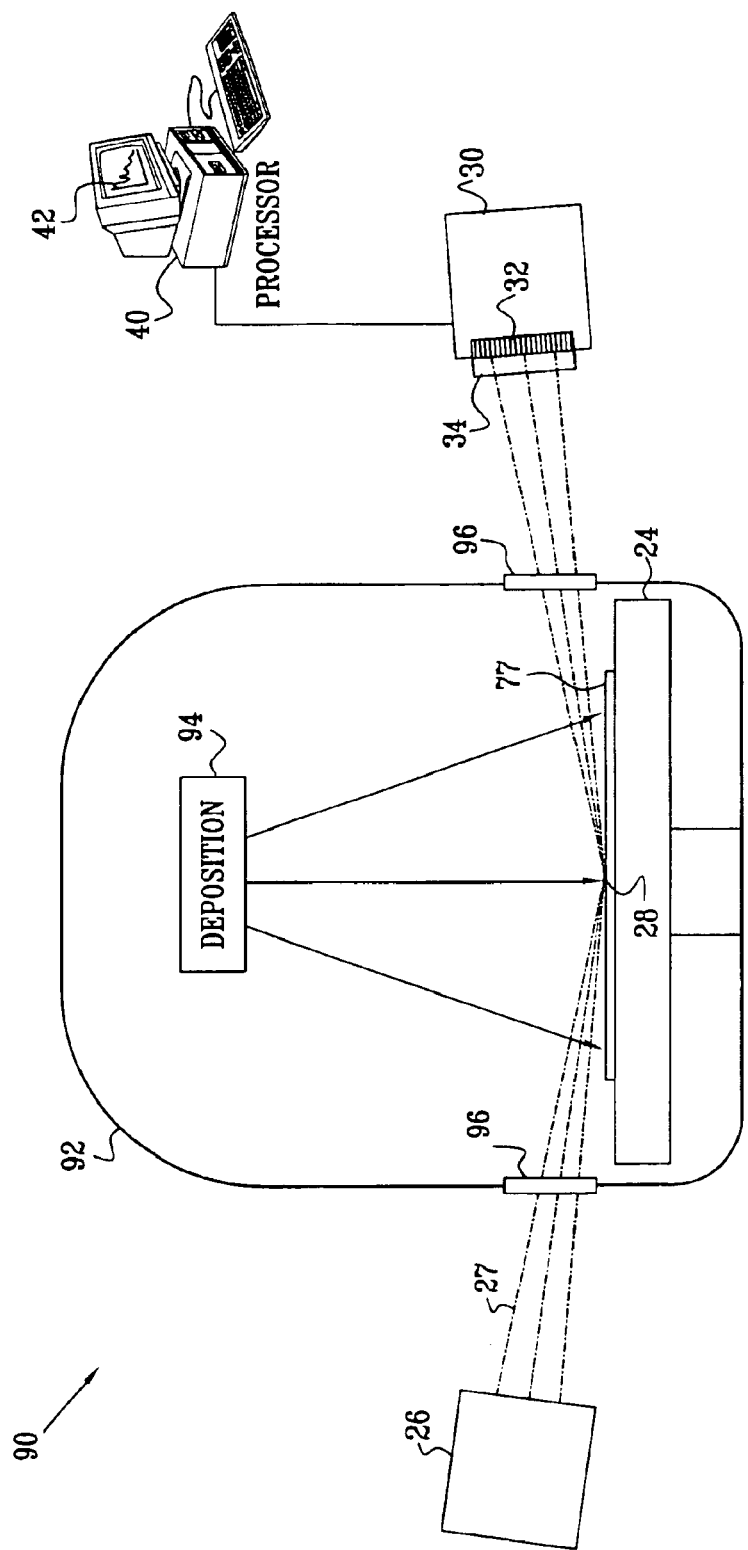
FIG. 7 is a schematic side view of a semiconductor processing chamber with X-ray inspection capability, in accordance with an embodiment of the present invention.

FIG. 7 is a schematic side view of a system 90 for semiconductor wafer fabrication and in situ inspection, in accordance with another embodiment of the present invention. System 90 comprises a vacuum chamber 92, containing deposition apparatus 94, for creating thin films on wafer 77, as is known in the art. The wafer is mounted on motion stage 24 within chamber 92. The chamber typically comprises X-ray windows 96, which may be of the type described in the above-mentioned Patent Application Publication US 2001/0043668 A1. X-ray source 26 irradiates area 28 on wafer 77 via one of windows 96, in the manner described above. The shutter, knife edge and slit shown in FIG. 1 are omitted from FIG. 7 for the sake of simplicity, but typically, elements of this sort are integrated into source 26 or within chamber 92.

X-rays reflected or scattered from area 28 are received by array 32 in detector assembly 30 via another one of windows 96. The array may typically be rotated between vertical and horizontal orientations, for performing either XRR or SAXRS measurements. Processor 40 receives signals from detector assembly 30, and processes the signals in order to assess characteristics of thin-film layers in production within chamber 92. The results of this assessment may be used in controlling deposition apparatus 94 so that the films produced by system 90 have desired characteristics, such as thickness, density and porosity.

Although the embodiments described above deal mainly with determining porosity characteristics of low-k dielectric layers on semiconductor wafers, the principles of the present invention can similarly be used in other X-ray reflectometry and scattering applications, as well as in other types of radiation-based analysis, using not only X-rays, but also other ionizing radiation bands. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. Apparatus for inspection of a sample, comprising:
   an X-ray source, which is adapted to emit a beam of X-rays so as to irradiate an area on a surface of the sample;
   a detector assembly, comprising an array of detector elements arranged to receive radiation from the surface due to irradiation of the area by the radiation source and to generate a signal responsive to the received radiation, the array having a first operative configuration for resolving the received radiation along a first axis perpendicular to the surface, and a second operative configuration for resolving the received radiation along a second axis parallel to the surface;
   X-ray optics, which are adapted to adjust a convergence angle of the beam depending upon whether the array is in the first or the second operative configuration; and
   a signal processor, which is coupled to process the signal from the detector assembly in the first configuration so as to determine a reflectance of the surface as a function of elevation angle relative to the surface, and to process the signal from the detector assembly in the second configuration so as to determine a scattering profile of the surface as a function of azimuthal angle in a plane of the surface.

2. The apparatus according to claim 1, wherein the X-ray optics are adapted to adjust a transverse dimension of the beam depending upon whether the array is in the first or the second operative configuration.

3. The apparatus according to claim 2, wherein the X-ray optics comprise a shutter assembly, which is adjustable so as to adjust a range of angles, relative to the surface of the sample, within which the beam of X-rays is incident on the surface.

4. The apparatus according to claim 3, wherein the signal processor is adapted to determine the scattering profile due to a surface layer that overlies a substrate of the sample, and wherein the shutter assembly is adjustable so that the range of angles within which the beam of X-rays is incident on the surface is approximately bounded by a first critical angle for total external reflection from the surface layer and by a second critical angle for total external reflection from the substrate, wherein the second critical angle is greater than the first critical angle.

5. The apparatus according to claim 1, wherein the array of detector elements has an array axis, and wherein the array is rotatable so that the array axis is perpendicular to the surface in the first operative configuration, and the array axis is parallel to the surface in the second operative configuration.

6. The apparatus according to claim 5, wherein the array comprises a linear array, and wherein the detector elements have a transverse dimension, perpendicular to the array axis, that is substantially greater than a pitch of the array.

7. The apparatus according to claim 5, wherein the array comprises a two-dimensional matrix of the detector elements, and wherein the detector assembly is adapted to bin the detector elements in respective rows of the array along a direction perpendicular to the array axis.

8. The apparatus according to claim 1, wherein the array comprises a two-dimensional matrix of the detector elements.

9. The apparatus according to claim 1, wherein the signal processor is adapted to determine the reflectance and the scattering profile due to a porous surface layer that overlies a substrate of the sample, and to estimate, based on the reflectance and the scattering profile, one or more characteristics of pores located within the porous surface layer.

10. The apparatus according to claim 9, wherein the one or more characteristics comprise a density and average size of the pores.

11. Apparatus for inspection of a sample, comprising:
an X-ray source, which is adapted to emit a beam of X-rays so as to irradiate an area on a surface of the sample;
a detector assembly, comprising an array of detector elements arranged to receive radiation from the surface due to irradiation of the area by the radiation source and to generate a signal responsive to the received radiation, the array having a first operative configuration for resolving the received radiation along a first axis perpendicular to the surface, and a second operative configuration for resolving the received radiation along a second axis parallel to the surface;
X-ray optics, which are adapted to adjust a transverse dimension of the beam depending upon whether the array is in the first or the second operative configuration; and
a signal processor, which is coupled to process the signal from the detector assembly in the first configuration so as to determine a reflectance of the surface as a function of elevation angle relative to the surface, and to process the signal from the detector assembly in the second configuration so as to determine a scattering profile of the surface as a function of azimuthal angle in a plane of the surface,
wherein the X-ray optics are adapted to adjust the beam so as to define a cone of rays, converging on the area on the surface of the sample, when the array is in the first operative configuration, and to substantially collimate the beam when the array is in the second operative configuration.

12. A method for inspection of a sample, comprising:
directing a beam of X-rays so as to irradiate an area on a surface of the sample;
configuring an array of detector elements in a first operative configuration to receive radiation from the surface due to irradiation of the area by the radiation source while resolving the received radiation along a first axis perpendicular to the surface, so as to generate a first signal responsive to the received radiation;
configuring the array of detector elements in a second operative configuration to receive the radiation from the surface due to irradiation of the area by the radiation source while resolving the received radiation along a second axis parallel to the surface, so as to generate a second signal responsive to the received radiation;
adjusting a convergence angle of the beam depending upon whether the array is in the first or the second operative configuration;
processing the first signal so as to determine a reflectance of the surface as a function of elevation angle relative to the surface; and
processing the second signal so as to determine a scattering profile of the surface as a function of azimuthal angle in a plane of the surface.

13. The method according to claim 12, wherein irradiating the area comprises adjusting a transverse dimension of the beam depending upon whether the array is in the first or the second operative configuration.

14. The method according to claim 13, wherein adjusting the transverse dimension comprises limiting the transverse dimension when the array is in the second operative configuration so that a range of angles within which the beam of X-rays is incident on the surface is approximately bounded by a first critical angle for total external reflection from a surface layer overlying a substrate of the sample and by a second critical angle for total external reflection from the substrate, wherein the second critical angle is greater than the first critical angle.

15. The method according to claim 14, wherein processing the first signal comprises determining the first and second critical angles, for use in adjusting the transverse dimension of the beam when the array is in the second operative configuration.

16. The method according to claim 12, wherein the array of detector elements has an array axis, and wherein configuring the array in the first operative configuration comprises aligning the array axis perpendicular to the surface in the first operative configuration, and wherein configuring the array in the second operative configuration comprises rotating the array so that the array axis is parallel to the surface in the second operative configuration.

17. The method according to claim 12, wherein the array comprises a two-dimensional matrix of the detector elements, and wherein configuring the array in the first operative configuration comprises binning the detector elements in respective lines of the array along a direction parallel to the surface, and configuring the array in the second operative configuration comprises binning the detector elements in the respective lines of the array along a direction perpendicular to the surface.

18. The method according to claim 12, wherein processing the first and second signals comprises determining the reflectance and the scattering profile due to a porous surface layer that overlies a substrate of the sample, and comprising estimating, based on the reflectance and the scattering profile, one or more characteristics of pores located within the porous surface layer.

19. The method according to claim 18, wherein the one or more characteristics comprise a density and average size of the pores.

20. The method according to claim 12, wherein irradiating the area comprises irradiating a semiconductor wafer within a chamber used to deposit a thin-film layer on the surface of the wafer, and wherein configuring the array of detector elements in the first and second operative configurations comprises receiving the radiation from the surface of the wafer within the chamber.

21. A method for inspection of a sample, comprising:
    irradiating an area on a surface of the sample;
    configuring an array of detector elements in a first operative configuration to receive radiation from the surface due to irradiation of the area by the radiation source while resolving the received radiation along a first axis perpendicular to the surface, so as to generate a first signal responsive to the received radiation;
    configuring the array of detector elements in a second operative configuration to receive the radiation from the surface due to irradiation of the area by the radiation source while resolving the received radiation along a second axis parallel to the surface, so as to generate a second signal responsive to the received radiation;
    processing the first signal so as to determine a reflectance of the surface as a function of elevation angle relative to the surface; and
    processing the second signal so as to determine a scattering profile of the surface as a function of azimuthal angle in a plane of the surface,
    wherein irradiating the area comprises directing a beam of X-rays toward the area, and adjusting a transverse dimension of the beam depending upon whether the array is in the first or the second operative configuration, and
    wherein directing the beam comprises directing a cone of rays to converge on the area when the array is in the first operative configuration, and wherein adjusting the transverse dimension comprises substantially collimating the beam when the array is in the second operative configuration.

22. A cluster tool for producing microelectronic devices, comprising:
    a deposition station, which is adapted to deposit a thin-film layer on a surface of a semiconductor wafer;
    an inspection station, comprising:
        an X-ray source, which is adapted to emit a beam of X-rays so as to irradiate an area on the surface of the wafer;
        a detector assembly, comprising an array of detector elements arranged to receive radiation from the surface due to irradiation of the area by the radiation source and to generate a signal responsive to the received radiation, the array having a first operative configuration for resolving the received radiation along a first axis perpendicular to the surface, and a second operative configuration for resolving the received radiation along a second axis parallel to the surface; and
        X-ray optics, which are adapted to adjust a convergence angle of the beam depending upon whether the array is in the first or the second operative configuration; and
    a signal processor, which is coupled to process the signal from the detector assembly in the first configuration so as to determine a reflectance of the surface as a function of elevation angle relative to the surface, and to process the signal from the detector assembly in the second configuration so as to determine a scattering profile of the surface as a function of azimuthal angle in a plane of the surface, so as to assess a quality of the thin-film layer deposited by the deposition station.

23. Apparatus for producing microelectronic devices, comprising:
    a production chamber, which is adapted to receive a semiconductor wafer;
    a deposition device, which is adapted to deposit a thin-film layer on a surface of the semiconductor wafer within the chamber;
    an X-ray source, which is adapted to emit a beam of X-rays so as to irradiate an area on the surface of the wafer within the chamber;
    a detector assembly, comprising an array of detector elements arranged to receive radiation from the surface due to irradiation of the area by the radiation source and to generate a signal responsive to the received radiation, the array having a first operative configuration for resolving the received radiation along a first axis perpendicular to the surface, and a second operative configuration for resolving the received radiation along a second axis parallel to the surface;
    X-ray optics, which are adapted to adjust a convergence angle of the beam depending upon whether the array is in the first or the second operative configuration; and
    a signal processor, which is coupled to process the signal from the detector assembly in the first configuration so as to determine a reflectance of the surf ace as a function of elevation angle relative to the surface, and to process the signal from the detector assembly in the second configuration so as to determine a scattering profile of the surface as a function of azimuthal angle in a plane of the surface, so as to assess a quality of the thin-film layer deposited by the deposition device.

* * * * *